(12) United States Patent
Arimoto (10) Patent No.: US 10,180,439 B2
(45) Date of Patent: *Jan. 15, 2019

(54) COCAINE APTAMER AND METHOD FOR DETECTING COCAINE USING THE SAME

(71) Applicant: Panasonic Intellectual Property Management Co., Ltd., Osaka (JP)

(72) Inventor: Satoshi Arimoto, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/601,040

(22) Filed: May 22, 2017

(65) Prior Publication Data

US 2018/0106819 A1    Apr. 19, 2018

(30) Foreign Application Priority Data

Oct. 13, 2016 (JP) .................................. 2016-201717

(51) Int. Cl.
| | |
|---|---|
| *C07H 21/02* | (2006.01) |
| *C07H 21/04* | (2006.01) |
| *G01N 33/94* | (2006.01) |
| *C12N 15/115* | (2010.01) |
| *C12Q 1/6804* | (2018.01) |

(52) U.S. Cl.
CPC .......... *G01N 33/946* (2013.01); *C12N 15/115* (2013.01); *C12Q 1/6804* (2013.01); *C12N 2310/16* (2013.01); *C12N 2310/3517* (2013.01)

(58) Field of Classification Search
CPC ............ C12Q 1/6825; C12Q 2525/205; C12N 15/111
See application file for complete search history.

(56) References Cited

U.S. PATENT DOCUMENTS

2013/0210023 A1* 8/2013 Tanner et al. ......... C12N 15/111

OTHER PUBLICATIONS

Du et al. (Anal. Chem., 2010, 82, 1556-1563).*
Wang et al. (Biosensors and Bioelectronics, 24, 2009, 3288-3292).*
James S. Swensen et al., "Continuous, Real-Time Monitoring of Cocaine in Undiluted Blood Serum via a Microfluidic, Electrochemical Aptamer-Based Sensor", Journal of American Chemical Society (Articles), 2009, vol. 131, pp. 4262-4266, Mar. 9, 2009.

* cited by examiner

*Primary Examiner* — Amy H Bowman
(74) *Attorney, Agent, or Firm* — McDermott Will & Emery LLP (57) ABSTRACT

The present invention provides a cocaine aptamer represented by the following chemical formula (Cl), R-DNA-L-Fc    (Cl)

where
R is selected from the group consisting of a hydrocarbon group and the derivative thereof;
DNA consists of a gene sequence capable of binding to cocaine;
L is a linker represented by $((CH_2)_2-O)_{n1}-PO_4-(CH_2)_{n2}-L1$;
L1 is absent or an optional linker;
n1 represents a natural number;
n2 represents a natural number; and
Fc represents a ferrocene group.
The cocaine aptamer is capable of detecting cocaine with high sensitivity.

18 Claims, 13 Drawing Sheets

Specification includes a Sequence Listing.

COCAINE APTAMER AND METHOD FOR DETECTING COCAINE USING THE SAME

INCORPORATION BY REFERENCE-SEQUENCE LISTING

The material contained in the ASCII text file named "P1003416US01_ST25.txt" created on Mar. 21, 2017 and having a file size of 510 bytes is incorporated by reference herein.

BACKGROUND

1. Technical Field

The present invention relates to a cocaine aptamer and a method for detecting cocaine using the same.

2. Description of the Related Art

Figure 11:
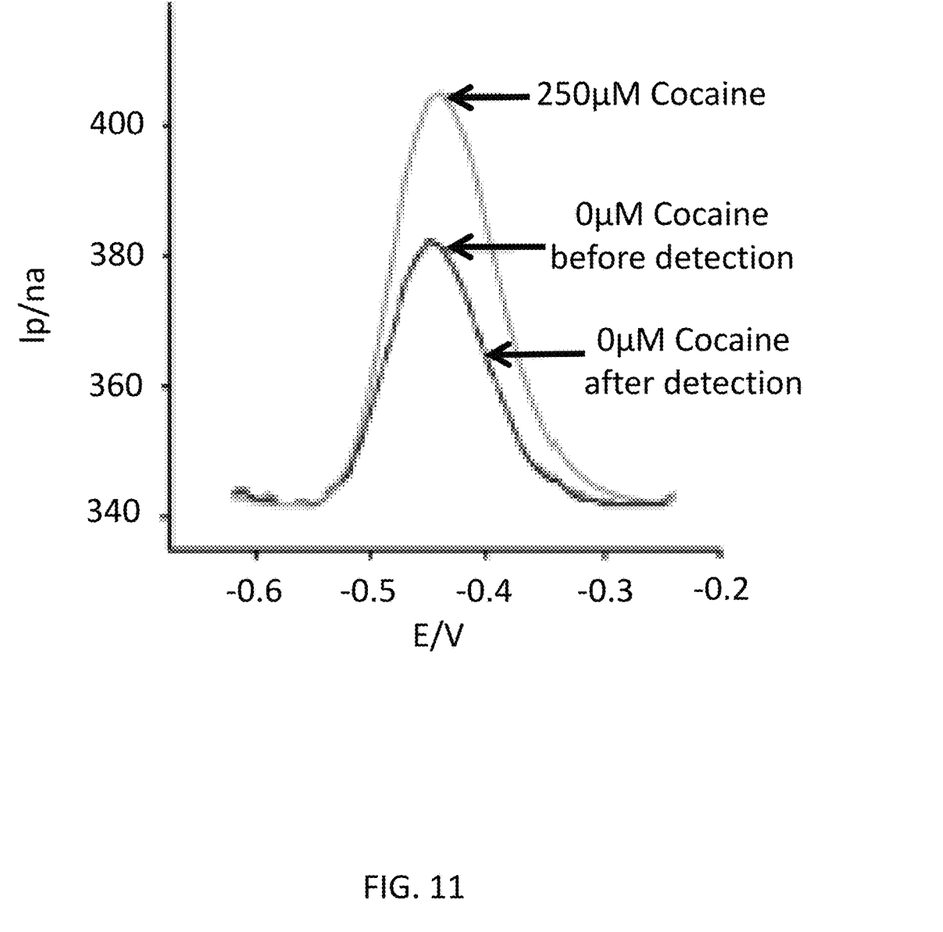
FIG. 11 is a duplicate of FIG. 3 included in James et. al.

James S. Swensen et al, "Continuous, Real-Time Monitoring of Cocaine in Undiluted Blood Serum via a Microfluidic, Electrochemical Aptamer-Based Sensor" Journal of American Chemical Society, 2009, 131, 4262-4266 (hereinafter, referred to as "James et. al.") discloses a cocaine aptamer represented by 5'-HS—$(CH_2)_{11}$-AGACAAGGAAAATCCTTCAATGAAGTGGGTCG-$(CH_2)_7$-MB-3' (SEQ ID NO: 01, MB represents methylene blue). FIG. 11 is a duplicate of FIG. 3 included in James et. al. As shown in FIG. 11, the reduction current of MB with regard to the cocaine aqueous solution having a concentration of 0 μM (namely, the aqueous solution which does not contain cocaine) is approximately 380 nanoampere. The reduction current of MB with regard to the cocaine aqueous solution having a concentration of 250 μM is approximately 400 nanoampere. Therefore, the S/N ratio of the cocaine aptamer disclosed in James et. al. is approximately 1.05 (=400/380).

SUMMARY

The present invention provides a cocaine aptamer represented by the following chemical formula (Cl), R-DNA-L-Fc  (Cl)

where
R is selected from the group consisting of a hydrocarbon group and the derivative thereof;
DNA consists of a gene sequence capable of binding to cocaine;
L is a linker represented by $((CH_2)_2—O)_{n1}—PO_4—(CH_2)_{n2}$-L1;
L1 is absent or an optional linker;
n1 represents a natural number;
n2 represents a natural number; and
Fc represents a ferrocene group.
The present invention provides a cocaine aptamer capable of detecting cocaine with high sensitivity.

DETAILED DESCRIPTION OF THE EMBODIMENT

Hereinafter, the embodiment of the present invention will be described.

(Cocaine Aptamer)

The cocaine aptamer according to the present embodiment is represented by the following chemical formula (Cl), R-DNA-L-Fc  (Cl)

where
R is selected from the group consisting of a hydrocarbon group and the derivatives thereof,
DNA consists of a gene sequence capable of binding to cocaine;
L is a linker represented by $((CH_2)_2—O)_{n1}—PO_4—(CH_2)_{n2}$-L1;
$L_1$ is absent or an optional linker;
n1 represents a natural number;
n2 represents a natural number; and
Fc represents a ferrocene group.
As disclosed in James et. al., an example of the gene sequence capable of binding to cocaine is (SEQ ID NO: 01)
AGACAAGGAAAATCCTTCAATGAAGTGGGTCG.

01).

As long as R is selected from the group consisting of a hydrocarbon group and the derivatives thereof, R is not limited. This is because R does not influence the detection of cocaine, as described later. An example of R is HS—$(CH_2)_{n3}$— (where n3 represents a natural number).

As is clear from the inventive examples and the comparative examples which will be described later, the cocaine aptamer according to the present embodiment is characterized by (I) $((CH_2)_2—O)_{n1}—PO_4$ group included in the linker L and (II) the ferrocene group Fc. Due to these two characteristics (I) and (II), the cocaine aptamer according to the present embodiment has high cocaine detection sensitivity.

As long as $L_1$ is absent or an optional linker, $L_1$ is not limited. This is because $L_1$ does not influence the detection of cocaine, as described later. Desirably, L1 is an amide bond (i.e., NHCO).

Desirably, n1 is a natural number of not less than 1 and not more than 20. More preferably, n1 is a natural number of not less than 3 and not more than 6. Desirably, n2 is a natural number of not less than 1 and not more than 20. More preferably, n2 is a natural number of not less than 3 and not more than 6.

(Fabricating Method of the Cocaine Aptamer)

Figure 1:
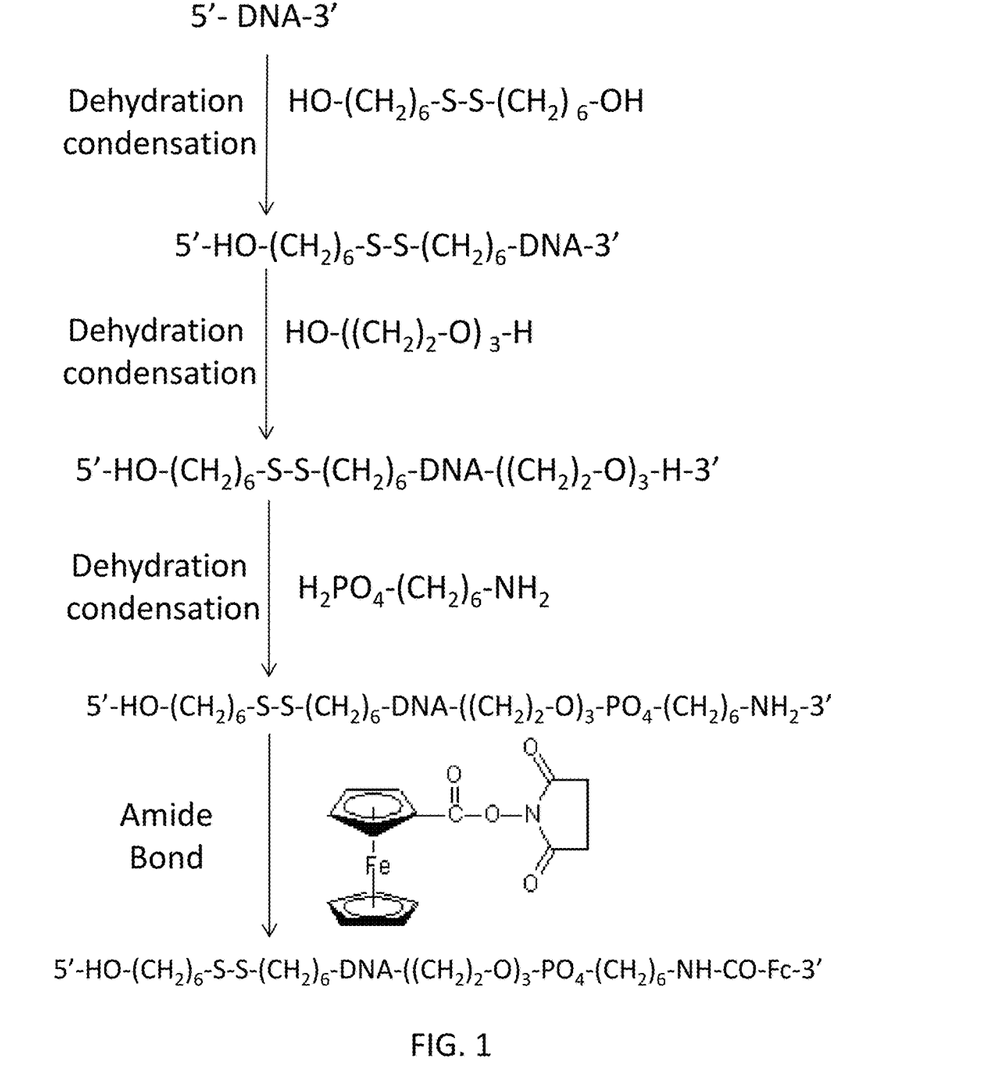
FIG. 1 is a part of a synthetic scheme of a cocaine aptamer according to the embodiment.
Figure 2:
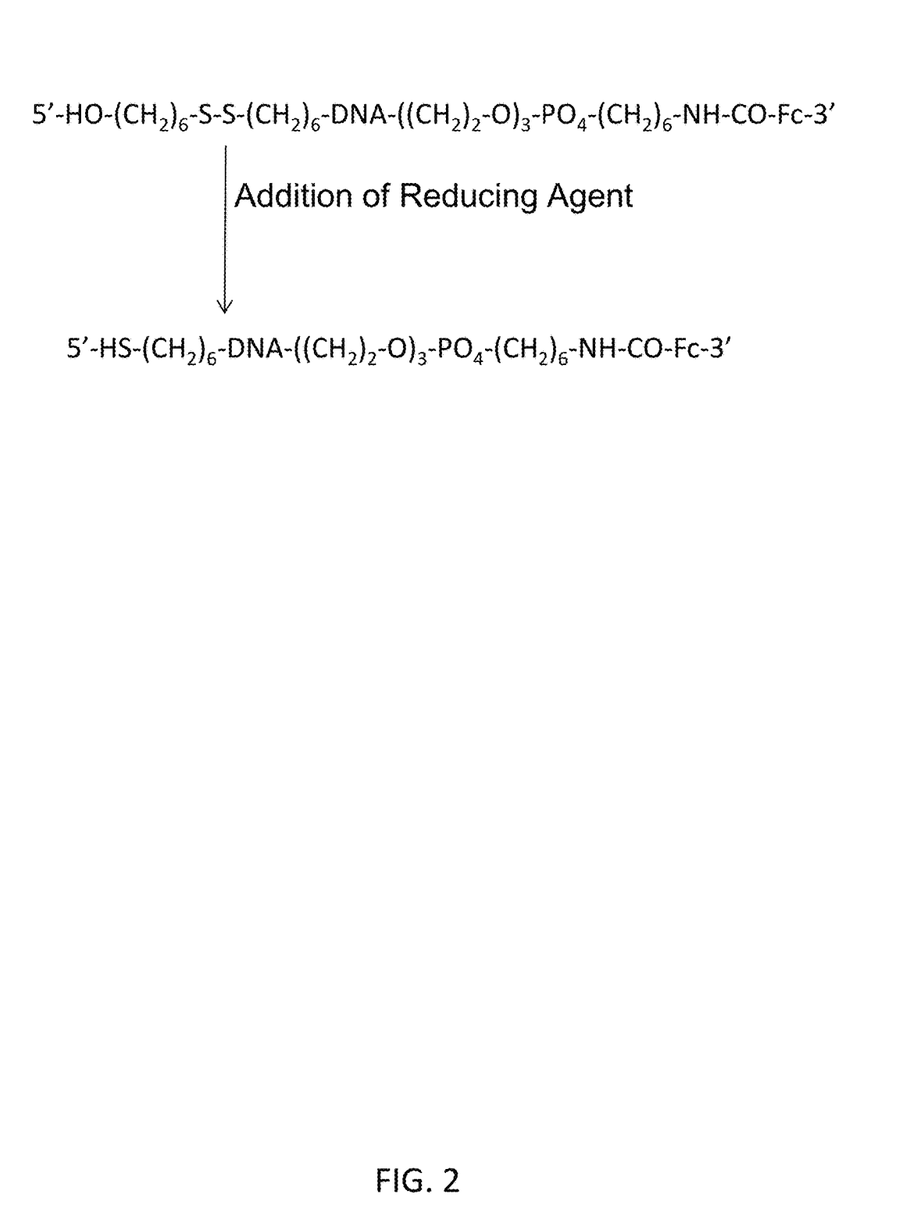
FIG. 2 is a part of the synthetic scheme of the cocaine aptamer according to the embodiment, subsequent to the synthetic scheme shown in FIG. 1.

Then, the fabricating method of the cocaine aptamer according to the present embodiment will be described. FIG. 1 and FIG. 2 show a synthetic scheme of the cocaine aptamer according to the present embodiment.

First, the gene sequence represented by (SEQ ID NO: 01)
AGACAAGGAAAATCCTTCAATGAAGTGGGTCG is synthesized by a typical artificial gene synthetic method. As described above, the gene sequence represented by SEQ ID NO: 01 is disclosed in James et. al.

Then, bis(hydroxyalkyl) disulfide (in FIG. 1, bis(6-hydroxy hexyl) disulfide represented by the chemical formula HO—$(CH_2)_6$—S—S—$(CH_2)_6$—OH) is added. In this way, the substituent including the disulfide group is connected to the 5' end of the gene sequence by dehydration condensation.

Polyglycol (in FIG. 1, triglycol represented by the chemical formula HO—$((CH_2)_2$—O$)_3$—H) is added. In this way, a part of L is connected to the 3' end of the gene sequence by dehydration condensation.

An amino alkyl phosphoric acid derivative (in FIG. 1, represented by the chemical formula $H_2PO_4$—$(CH_2)_6$—$NH_2$) is added. In this way, a part of L is connected to the end of the polyglycol by dehydration condensation so as to extend the 3' end of the gene sequence. The amino alkyl phosphoric acid derivative is obtained by dehydration condensation of phosphoric acid and alkanolamine. The amino alkyl phosphoric acid derivative represented by the chemical formula $H_2PO_4$—$(CH_2)_6$—$NH_2$ is obtained by dehydration condensation of phosphoric acid and 6-amino-1-hexanol.

A ferrocene group Fc derivative (in FIG. 1, a ferrocene group Fc-COO-succinimide) is added. In this way, the ferrocene group Fc is connected to the end of the phosphoric acid derivative by amide bond so as to further extend the 3' end of the gene sequence.

As shown in FIG. 2, the disulfide group is cut using a reducing agent. In this way, the cocaine aptamer represented by the chemical formula R-DNA-L-ferrocene group Fc (C1) is provided. An example of the reducing agent is Tris-(2-carboxyethyl) phosphine hydrochloride (hereinafter, referred to as "TCEP").

In FIG. 2,

R is represented by HS—$(CH_2)_6$—; and

L is a linker represented by $((CH_2)_2$—O$)_{n1}$—$PO_4$—$(CH_2)_{n2}$-L1 (i.e., n1 is equal to 3, n2 is equal to 6, and L1 is an amide bond represented by NHCO).

The cocaine aptamer according to the present embodiment can be synthesized by Nihon Gene Research Laboratories, Inc.

(Using Method of the Cocaine Aptamer)

Hereinafter, a method for detecting cocaine contained in a sample solution using the cocaine aptamer according to the present embodiment by will be described. In other words, a method for determining whether or not a sample solution contains cocaine using the cocaine aptamer according to the present embodiment will be described.

(Step (a))

First, the cocaine aptamer according to the present embodiment is mixed with a sample solution. In this way, a mixture solution is prepared. It is desirable that the sample solution is an aqueous solution. It is desirable that the cocaine aptamer according to the present embodiment is a single-stranded chain. For this reason, it is desirable that the cocaine aptamer according to the present embodiment is subject to heat treatment before the cocaine aptamer according to the present embodiment is mixed with the sample solution. As one example of the heat treatment, the cocaine aptamer according to the present embodiment is heated at 80 degrees Celsius for five minutes and then cooled to 25 degrees Celsius for thirty minutes. In this way, a single-stranded cocaine aptamer is obtained.

(Step (b))

In the step (b), restriction enzyme exonuclease III is added to the mixture solution prepared in the step (a). Restriction enzyme exonuclease III is the 3' to 5' exonuclease specific for a double-stranded deoxyribonucleic acid and releases 5'-mononucleotide from the 3'-OH end of the double strand deoxyribonucleic acid. When the sample solution contains cocaine, the cocaine aptamer binds to cocaine so as to form a double-stranded chain. Therefore, the DNA which has bound to cocaine is decomposed by the restriction enzyme exonuclease III. Due to the decomposition of the DNA, a part of the cocaine aptamer including the ferrocene group Fc is liberated in the mixture solution. Due to the decomposition of the DNA, the substituent R is liberated in the mixture solution; however, the substituent R does not influence the ferrocene group Fc. Therefore, the substituent R is not limited. Similarly, $L_1$ is not limited unless $L_1$ influences the ferrocene group Fc.

On the other hand, when the sample solution does not contain cocaine, the cocaine aptamer hardly forms double-stranded chain. Therefore, even if after the restriction enzyme exonuclease III is added, the cocaine aptamer according to the present embodiment does not change and the part of the cocaine aptamer including the ferrocene group Fc is not liberated.

It is desirable to deactivate the restriction enzyme exonuclease III at the end of the step (b). Specifically, ethylenediaminetetraacetic acid (hereinafter, referred to as "EDTA") is added to the mixture solution.

(Step (c))

In the step (c), reduction current of the ferrocene group Fc included in the part of the cocaine aptamer liberated in the step (b) is measured by a cyclic voltammetry method using a potentiostat. Since the ferrocene group Fc is a reductant, the reduction current RC1 of the ferrocene group Fc is measured in the cyclic voltammetry according to the present embodiment, while an oxidation potential is changed continuously. Specifically, first, the oxidation potential is increased from 0 volts to 0.6 volts. Then, the oxidation potential is decreased from 0.6 volts to 0 volts. The reduction potential of this period is set to 0 volts during this period. In other words, the reduction potential is set to 0 volts during this period, regardless of the change of the oxidation potential.

Cocaine is detected on the basis of the measured reduction current RC1 of the ferrocene group Fc with regard to the predetermined oxidation potential (e.g., 0.5 volts). Hereinafter, the method for determining whether or not the sample solution contains cocaine will be described in more detail.

(Step (d))

When the following mathematical formula (M1) is satisfied, it is determined that the sample solution contains cocaine.

$$RC1/RC2 > 1.0 \qquad \text{(M1)}$$

where

RC2 represents reduction current of the ferrocene group Fc measured in advance with regard to the predetermined oxidation potential (e.g., 0.5 volts) of the sample solution which does not contain cocaine.

The value of RC2 is measured as below. The reduction current of the ferrocene group Fc contained in the mixture solution which does not contain cocaine is measured as a value of background noise by the cyclic voltammetry method using the potentiostat. The value of RC2 is measured in advance before the method according to the present embodiment is carried out.

Needless to say, when the ferrocene group Fc is not liberated in the mixture solution contained in the cocaine aptamer in the step (b) (namely, the sample solution does not contain cocaine), an equation RC1=RC2 (i.e., RC1/RC2=1) is established. In other words, the ferrocene group Fc included in the cocaine aptamer in which the gene sequence (typically, represented by SEQ ID NO: 01) is not decomposed does not contribute to an increase of the value of the reduction current RC1.

As is clear from the inventive examples and the comparative examples which will be described later, cocaine is detected with higher sensitivity in a case of using the ferrocene group Fc than in a case of using MB (MB represents methylene blue). Furthermore, since the linker L includes $((CH_2)_2-O)_{n1}-PO_4$, cocaine is detected with higher sensitivity.

EXAMPLES

Hereinafter, the present invention will be described in more detail with reference to the examples. In the following examples, the DNA consists of the gene sequence represented by SEQ ID NO: 01.

Inventive Example 1

The inventive example 1 is composed of the inventive example 1A (cocaine concentration: 250 μM) and inventive example 1B (cocaine concentration: 0 μM).

The cocaine aptamer represented by the following chemical formula (C1a) was synthesized by Nihon Gene Research Laboratories, Inc.

$$5'-HS-(CH_2)_6-DNA-((CH_2)_2-O)_3-PO_4-(CH_2)_6-NH-CO\text{-Ferrocene group Fc-}3' \quad (C1a)$$

First, a mixed solvent was prepared. The mixed solvent contained 20 mM of Tris-HCl, 140 mM of NaCl, 5 mM of KCl, and 5 mM of $MgCl_2$.

Inventive Example 1A

Cocaine was added to the mixed solvent to provide a mixture solution. The concentration of the cocaine was 250 μM. Then, the above-mentioned cocaine aptamer (concentration: 10 μM) was added to the mixture solution.

Then, the mixture solution was subject to heat treatment. Specifically, the aqueous solution containing the cocaine aptamer was heated at 80 degrees Celsius for five minutes. Then, the aqueous solution was cooled to 25 degrees Celsius for thirty minutes. Due to the heat-treatment, the cocaine aptamer was liberated in the mixture solutions as a single-stranded cocaine aptamer, and then the cocaine aptamer bound to cocaine so as to form a double-stranded chain together with cocaine.

Restriction enzyme exonuclease III having a concentration of 2 unit/100 μL was added to the mixture solution. The mixture solution was stirred for ten seconds. The cocaine aptamer which had bound to cocaine so as to form the double-stranded chain was decomposed by the restriction enzyme exonuclease III. As a result, a part of the cocaine aptamer including the ferrocene group Fc was liberated.

Then, EDTA having a concentration of 50 mM was added to the mixture solution to deactivate the restriction enzyme exonuclease III.

Reduction current of the ferrocene group Fc included in the part of the liberated cocaine aptamer was measured using a potentiostat by a cyclic voltammetry method. A plate-like measurement electrode (available from BAS Inc., trade name: Comb-shaped electrode Au) was connected to the potentiostat. The plate-like measurement electrode had two comb-shaped electrodes engaged with each other on the surface thereof. Each of the comb-shaped electrode was composed of one long electrode and a lot of needle electrodes. Each of the needle electrodes was extended from the one long electrode so as to be perpendicular to the one long electrode. One comb-shaped electrode was used as an oxidation electrode, whereas the other comb-shaped electrode was used as a reduction electrode. The total number of the needle electrodes included in the two comb-shaped electrodes was 130 (=65×2). A width of one needle electrode was 2 micrometers. The distance between adjacent two needle electrodes was also 2 micrometers. A reference electrode of Ag/AgCl was connected to the potentiostat.

In the cyclic voltammetry method, the oxidation potential was increased from 0 volts to 0.6 volts at speed of 10 mV/s. Then, at the same speed, the oxidation potential was decreased from 0.6 volts to 0 volts. The mixture solution was swept by the cyclic voltammetry method by changing the oxidation potential in this way. The reduction potential was set to 0 volts.

Figure 3:
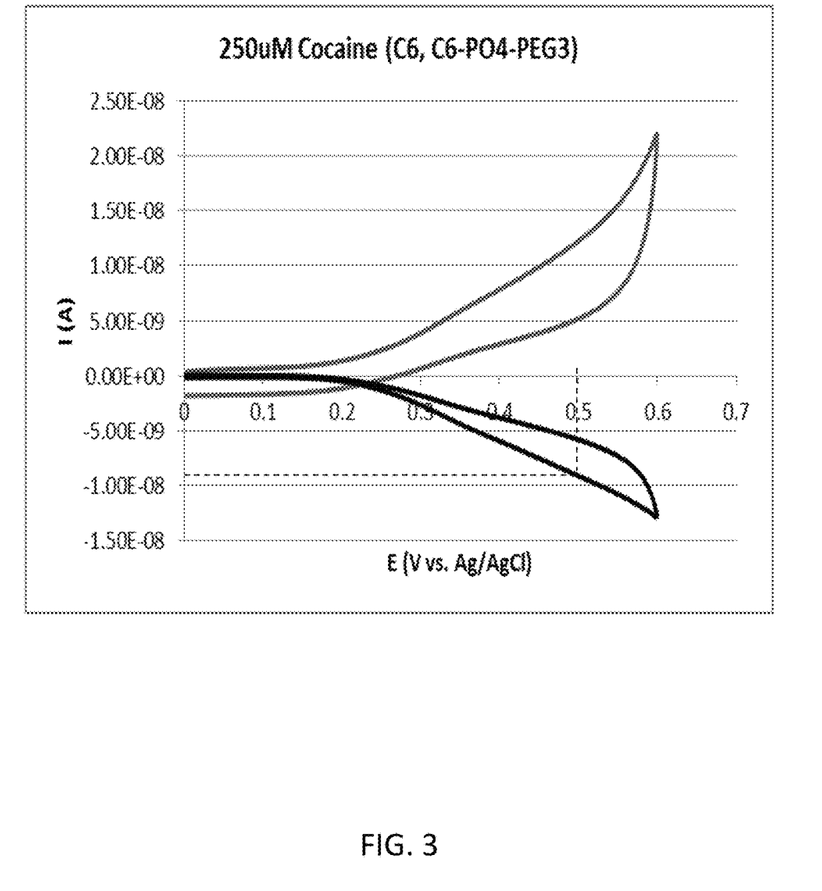
FIG. 3 shows a cyclic voltammogram according to the inventive example 1A (cocaine concentration: 250 μM).

FIG. 3 shows the cyclic voltammogram according to the inventive example 1A. As shown in FIG. 3, the reduction current RC1 with regard to the oxidation potential of 0.5 volts was approximately 9.09 nanoampere.

Inventive Example 1B

Figure 4:
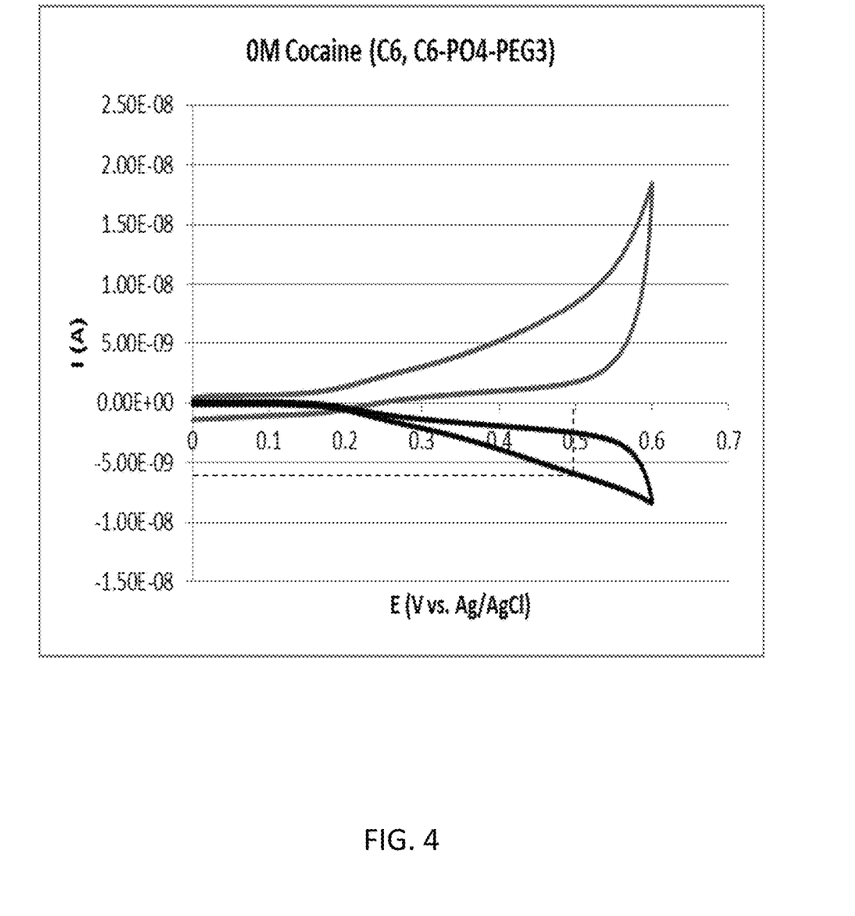
FIG. 4 shows a cyclic voltammogram according to the inventive example 1B (cocaine concentration: 0 μM).

In the inventive example 1B, an experiment similar to the inventive example 1A was conducted, except that cocaine was not added to the mixed solvent. In other words, in the inventive example 1B, the concentration of cocaine was 0 μM. FIG. 4 shows the cyclic voltammogram according to the inventive example 1B. As shown in FIG. 4, the reduction current RC2 with regard to the oxidation potential of 0.5 volts was approximately 5.93 nanoampere. Therefore, in the inventive example 1, the value of RC1/RC2 with regard to the oxidation potential of 0.5 volts was 1.53.

Inventive Example 2

In the inventive example 2, an experiment similar to the inventive example 1 was conducted, except that the cocaine aptamer represented by the following chemical formula (C1b) was used in place of the cocaine aptamer represented by the chemical formula (C1a).

$$5'-HS-(CH_2)_6-DNA-((CH_2)_2-O)_6-PO_4-(CH_2)_6-NH-CO\text{-Ferrocene group Fc-}3' \quad (C1b)$$

The cocaine aptamer represented by the chemical formula (C1b) was synthesized by Nihon Gene Research Laboratories, Inc.

Figure 5:
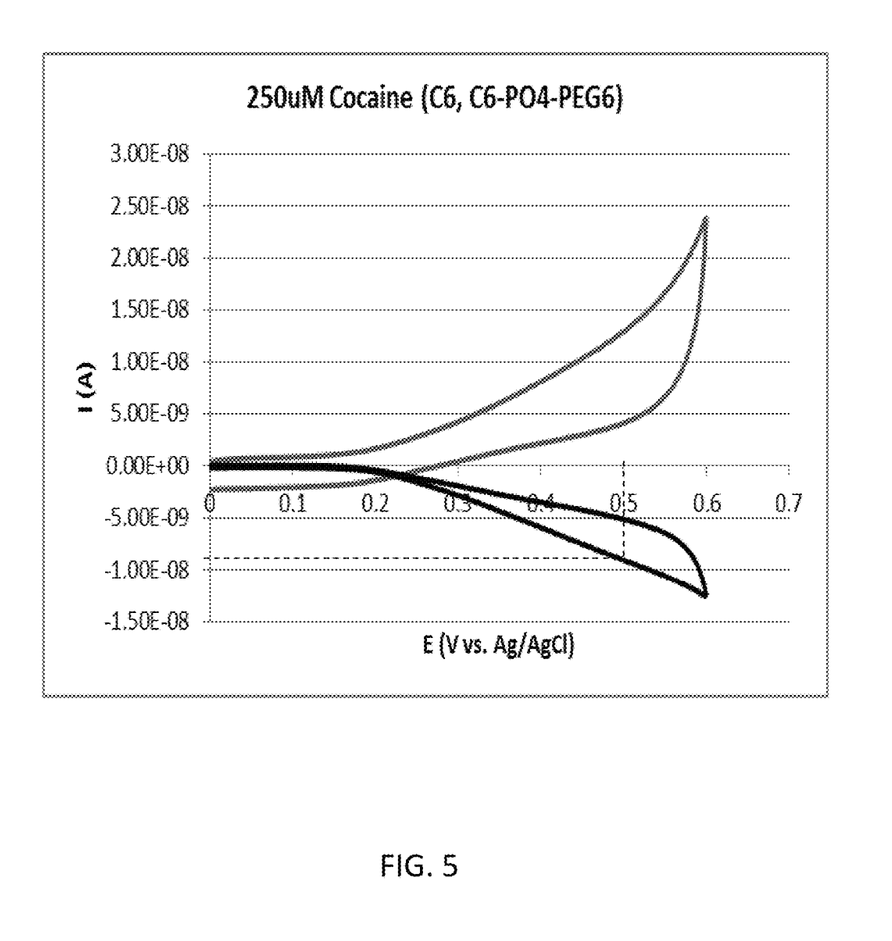
FIG. 5 shows a cyclic voltammogram according to the inventive example 2A (cocaine concentration: 250 μM).

FIG. 5 shows a cyclic voltammogram according to the inventive example 2A (cocaine concentration: 250 μM). As shown in FIG. 5, the reduction current RC1 with regard to the oxidation potential of 0.5 volts was approximately 9.01 nanoampere.

Figure 6:
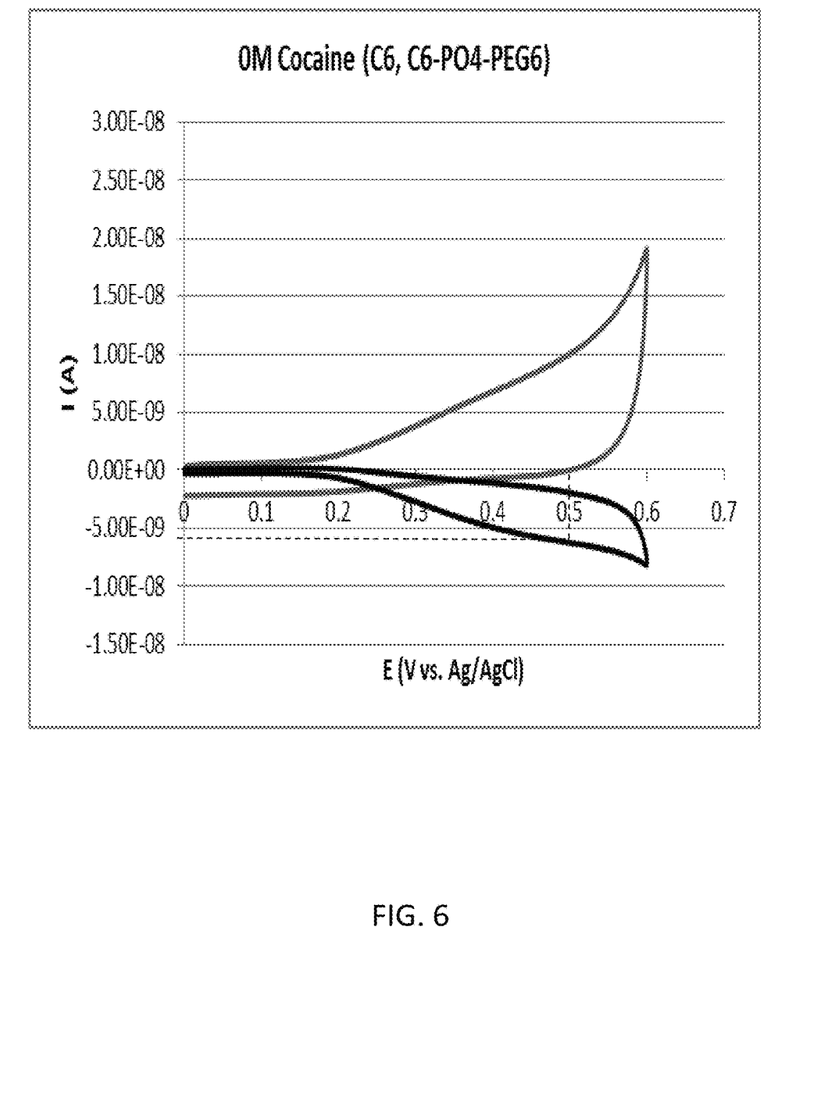
FIG. 6 shows a cyclic voltammogram according to the inventive example 2B (cocaine concentration: 0 μM).

FIG. 6 shows a cyclic voltammogram according to the inventive example 2B (cocaine concentration: 0 μM). As shown in FIG. 6, the reduction current RC2 with regard to the oxidation potential of 0.5 volts was approximately 6.23 nanoampere.

Therefore, in the inventive example 2, the value of RC1/RC2 with regard to the oxidation potential of 0.5 volts was 1.45.

Comparative Example 1

In the comparative example 1, an experiment similar to the inventive example 1 was conducted, except that the cocaine aptamer represented by the following chemical formula (Clc) was used in place of the cocaine aptamer represented by the chemical formula (Cla).

5'-HS—(CH$_2$)$_6$-DNA-(CH$_2$)$_6$—NH—CO— Ferrocene group Fc-3'  (Clc)

The cocaine aptamer represented by the chemical formula (Clc) was synthesized by Nihon Gene Research Laboratories, Inc.

Figure 7:
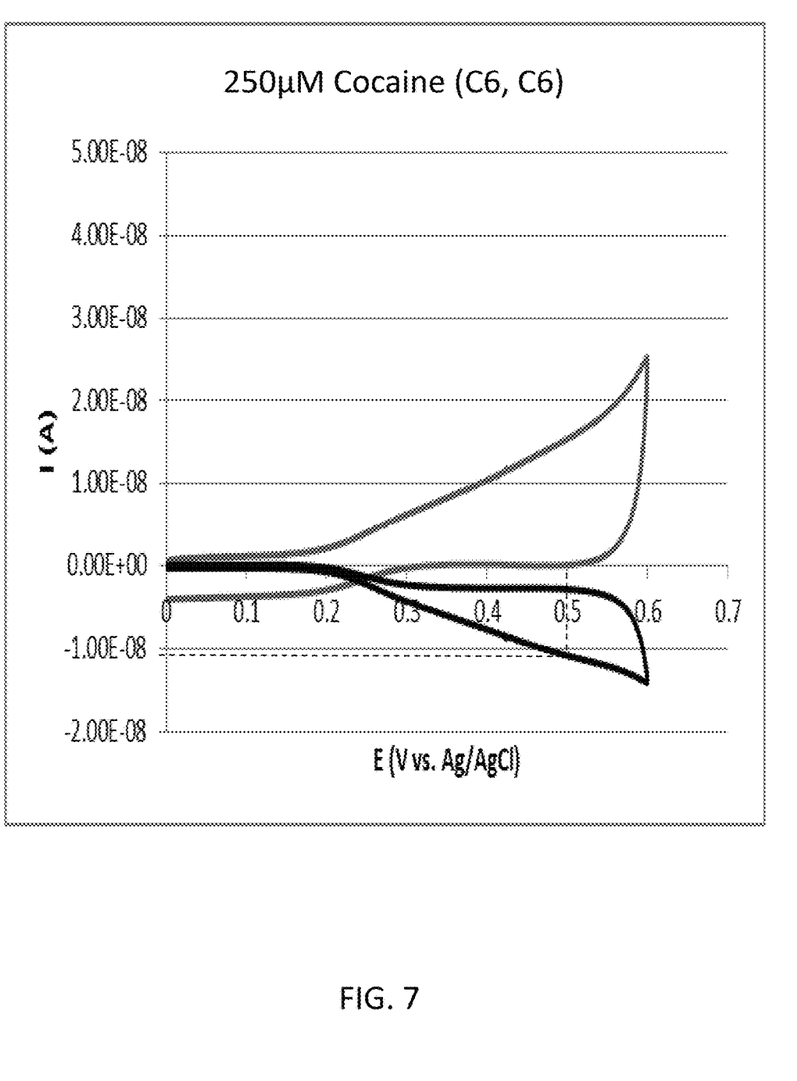
FIG. 7 shows a cyclic voltammogram according to the comparative example 1A (cocaine concentration: 250 μM).

FIG. 7 shows a cyclic voltammogram according to the comparative example 1A (cocaine concentration: 250 μM). As shown in FIG. 7, the reduction current RC1 with regard to the oxidation potential of 0.5 volts was approximately 10.08 nanoampere.

Figure 8:
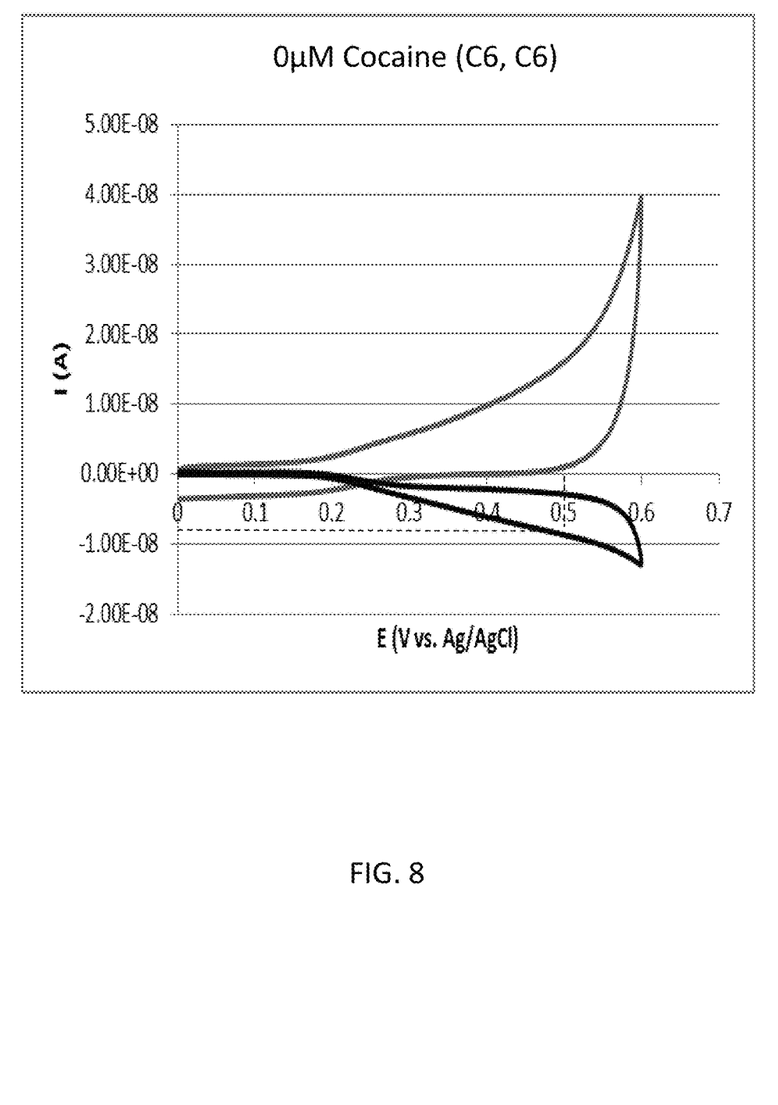
FIG. 8 shows a cyclic voltammogram according to the comparative example 1B (cocaine concentration: 0 μM).

FIG. 8 shows a cyclic voltammogram according to the comparative example 1B (cocaine concentration: 0 μM). As shown in FIG. 8, the reduction current RC2 with regard to the oxidation potential of 0.5 volts was approximately 8.67 nanoampere.

was identical to the cocaine aptamer disclosed in James et. al. and synthesized in accordance with the disclosure of James. et. al.

5'-HS—(CH$_2$)$_{11}$-DNA-(CH$_2$)$_7$—NH—CO-MB-3'  (Cld)

where
MB represents methylene blue.

(II) Since methylene blue is an oxidant, oxidation current was measured in the cyclic voltammetry method in place of the reduction current.

Figure 9A:
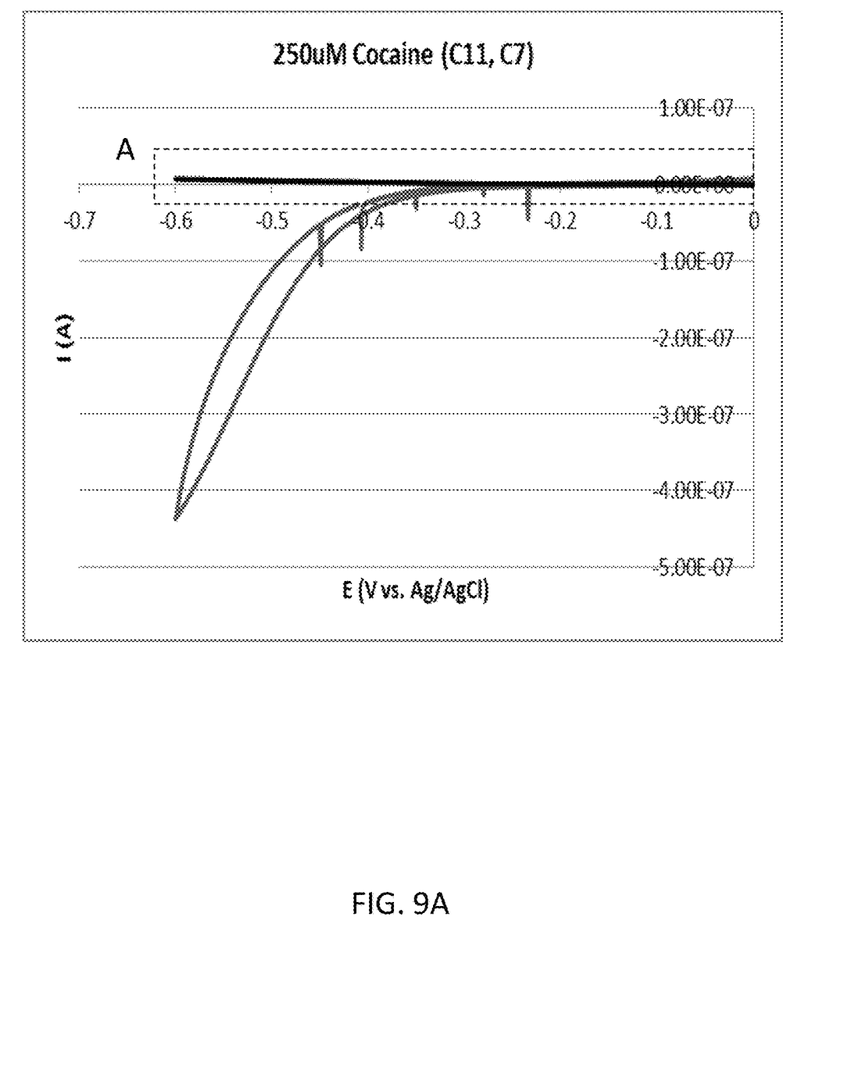
FIG. 9A shows a cyclic voltammogram according to the comparative example 2A (cocaine concentration: 250 μM).
Figure 9B:
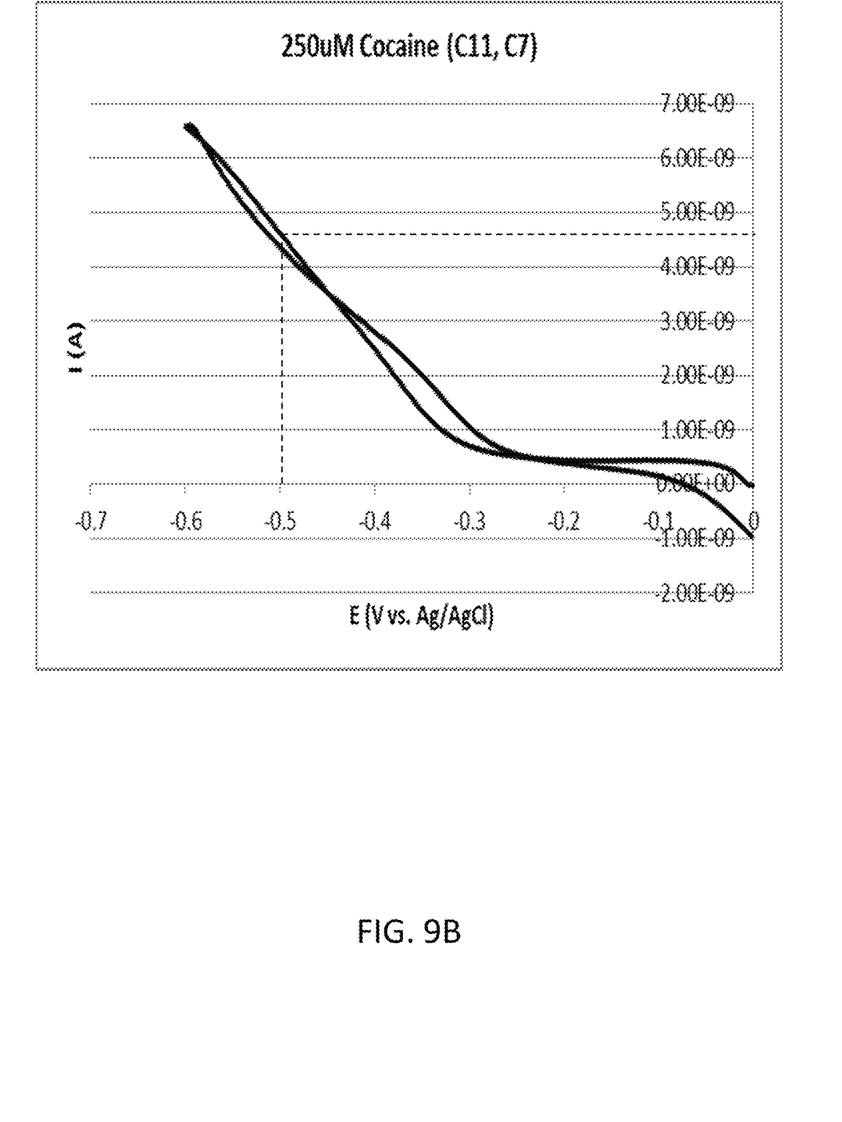
FIG. 9B shows an enlarged view of a part surrounded by a dashed line A included in FIG. 9A.

FIG. 9A shows a cyclic voltammogram according to the comparative example 2A (cocaine concentration: 250 μM). FIG. 9B shows an enlarged view of a part surrounded by a dashed line A included in FIG. 9A. As shown in FIG. 9B, the oxidation current with regard to the reduction potential of −0.5 volts was approximately 4.62 nanoampere.

Figure 10A:
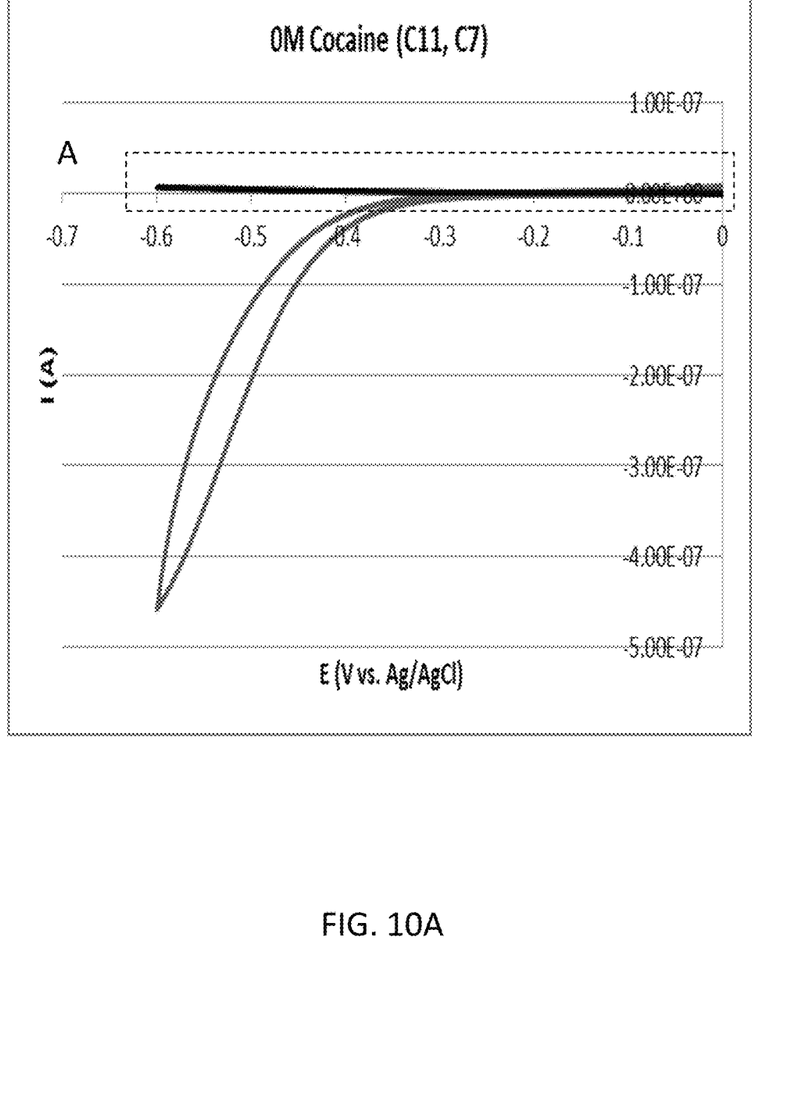
FIG. 10A shows a cyclic voltammogram according to the comparative example 2B (cocaine concentration: 0 μM).
Figure 10B:
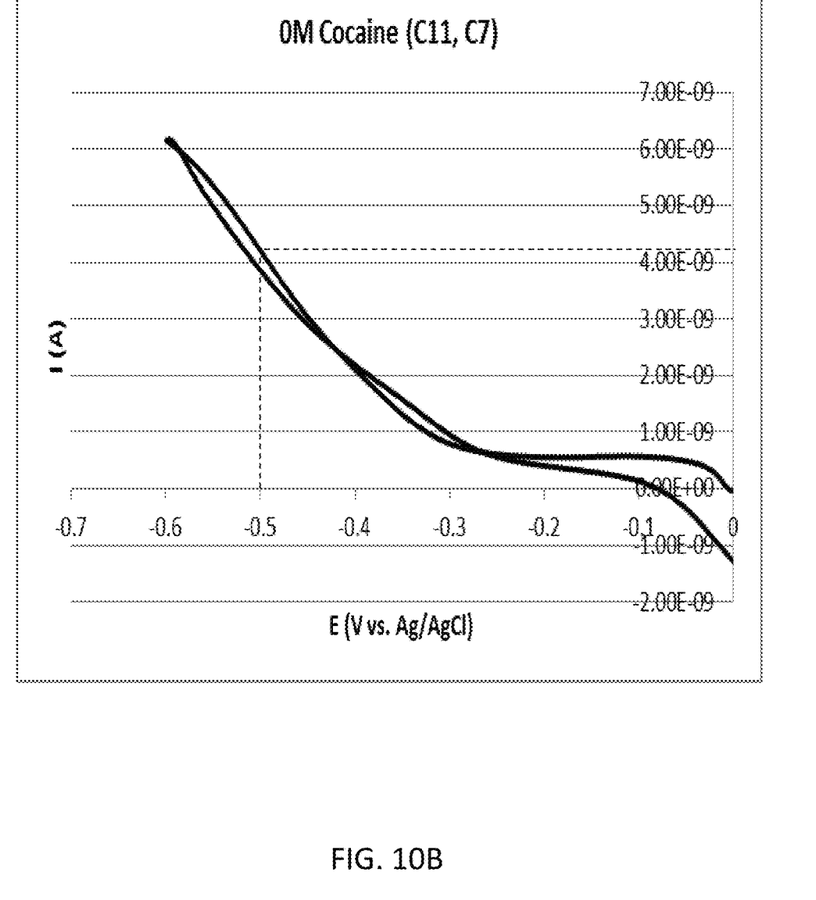
FIG. 10B shows an enlarged view of a part surrounded by a dashed line A included in FIG. 10A.

FIG. 10A shows a cyclic voltammogram according to the comparative example 2B (cocaine concentration: 0 μM). FIG. 10B shows an enlarged view of a part surrounded by a dashed line A included in FIG. 10A. As shown in FIG. 10B, the oxidation current with regard to the reduction potential of −0.5 volts was approximately 4.20 nanoampere.

Therefore, in the comparative example 2, the ratio of the two oxidation currents measured with regard to the reduction potential of −0.5 volts was approximately 1.10 (=4.62/4.20).

As is clear from the comparison of the inventive examples 1-2 with the comparative example 1, the linker L including ((CH$_2$)$_2$—O)$_{n1}$—PO$_4$ improves the detection sensitivity of cocaine.

As is clear from the comparison of the inventive examples 1-2 with the comparative example 2, the ferrocene group Fc improves the detection sensitivity of cocaine.

INDUSTRIAL APPLICABILITY

The present invention can be used for detection of cocaine.

SEQUENCE LISTING

```
<160> NUMBER OF SEQ ID NOS: 1

<210> SEQ ID NO 1
<211> LENGTH: 32
<212> TYPE: DNA
<213> ORGANISM: Artificial Sequence
<220> FEATURE:
<223> OTHER INFORMATION: DNA Aptamer capable of binding to cocaine

<400> SEQUENCE: 1
agacaaggaa aatccttcaa tgaagtgggt cg                                 32
```

Therefore, in the comparative example 1, the value of RC1/RC2 with regard to the oxidation potential of 0.5 volts was 1.24.

Comparative Example 2

In the comparative example 2, an experiment similar to the inventive example 1 was conducted, except for the following two matters (I) and (II).

(I) The cocaine aptamer represented by the following chemical formula (Cld) was used in place of the cocaine aptamer represented by the chemical formula (Cla). The cocaine aptamer represented by the chemical formula (Cld)

The invention claimed is:

1. A cocaine aptamer represented by the following chemical formula (CI),

R-DNA-L-Fc  (CI)

where
R comprises a hydrocarbon group;
DNA includes a gene sequence capable of binding to cocaine, wherein the gene sequence is represented by (SEQ ID NO: 01)
AGACAAGGAAAATCCTTCAATGAAGTGGGTCG;

L is a linker represented by ((CH$_2$)$_2$—O)$_{n1}$—PO$_4$—(CH$_2$)$_{n2}$-L1;

L1 is absent or an optional linker;
n1 represents a natural number;
n2 represents a natural number; and
Fc represents a ferrocene group.

2. The cocaine aptamer according to claim 1, wherein n1 is a natural number of not less than 1 and not more than 20 and n2 is a natural number of not less than 1 and not more than 20.

3. The cocaine aptamer according to claim 1, wherein R is represented by HS—(CH$_2$)$_{n3}$—
where
n3 represents a natural number.

4. The cocaine aptamer according to claim 1, wherein n1 is an integer not less than 3 and not more than 6.

5. The cocaine aptamer according to claim 1, wherein L1 represents an amide bond.

6. A method for detecting cocaine contained in a sample solution, the method comprising:
   (a) mixing a cocaine aptamer according to claim 1 with the sample solution to prepare a mixture solution;
   (b) adding restriction enzyme exonuclease III to the mixture solution prepared in the step (a); and
   (c) measuring the mixture solution electrochemically to detect cocaine after the step (b).

7. The method according to claim 6, wherein
in the step (b), a part of the cocaine aptamer including the ferrocene group Fc is liberated in the mixture solution.

8. The method according to claim 6, wherein
in the step (c), a concentration of the ferrocene group Fc included in the part of the cocaine aptamer liberated in the step (b) is measured.

9. The method according to claim 6, wherein n1 is a natural number of not less than 1 and not more than 20 and n2 is a natural number of not less than 1 and not more than 20.

10. The method according to claim 6, wherein R is represented by HS—(CH$_2$)$_{n3}$—
where
n3 represents a natural number.

11. The method according to claim 6, wherein n1 is an integer not less than 3 and not more than 6.

12. The method according to claim 6, wherein L1 represents an amide bond.

13. A method for determining whether or not a sample solution contains cocaine; the method comprising:
   (a) mixing a cocaine aptamer according to claim 1 with the sample solution to prepare a mixture solution;
   (b) adding restriction enzyme exonuclease III to the mixture solution prepared in the step (a);
   (c) measuring a reduction current RC1 of the ferrocene group Fc with regard to a predetermined oxidation potential by a cyclic voltammetry method after the step (b); and
   (d) determining that the sample solution contains the cocaine, if the following mathematical formula (M1) is satisfied, $$RC1/RC2 > 1.0 \quad (M1)$$

where
RC2 represents a reduction current of the ferrocene group Fc measured in advance with regard to the predetermined oxidation potential of a sample solution which does not contain cocaine.

14. The method according to claim 13, wherein
in the step (b), a part of the cocaine aptamer including the ferrocene group Fc is liberated in a mixture solution.

15. The method according to claim 13, wherein n1 is a natural number of not less than 1 and not more than 20 and n2 is a natural number of not less than 1 and not more than 20.

16. The method according to claim 13, wherein R is represented by HS—(CH$_2$)$_{n3}$—
where
n3 represents a natural number.

17. The method according to claim 13, wherein n1 is an integer not less than 3 and not more than 6.

18. The method according to claim 13, wherein L1 represents an amide bond.

* * * * *